(12) United States Patent
Tanaka et al.

(10) Patent No.: US 6,676,034 B2
(45) Date of Patent: Jan. 13, 2004

(54) ATOMIZER AND INHALATOR USING SAME

(75) Inventors: Shinya Tanaka, Kyoto (JP); Takao Terada, Kyoto (JP)

(73) Assignee: Omron Corporation, Kyoto (JP)

( * ) Notice: Subject to any disclaimer, the term of this patent is extended or adjusted under 35 U.S.C. 154(b) by 98 days.

(21) Appl. No.: 10/007,801

(22) Filed: Nov. 6, 2001

(65) Prior Publication Data

US 2002/0074426 A1 Jun. 20, 2002

(30) Foreign Application Priority Data

Nov. 11, 1999  (JP) .......................................... 11-0337028

(51) Int. Cl.[7] ................................................. B05B 1/08
(52) U.S. Cl. ................................ 239/102.1; 239/102.2; 239/600
(58) Field of Search ..................... 239/102.1, 102.2, 239/4, 600; 128/200.14, 200.16; 310/314–316

(56) References Cited

U.S. PATENT DOCUMENTS 5,518,179 A * 5/1996 Humberstone et al. .. 239/102.2
5,657,926 A * 8/1997 Toda ........................ 239/102.2
6,293,474 B1 * 9/2001 Helf et al. ................ 239/102.2

* cited by examiner

Primary Examiner—Steven J. Ganey
(74) Attorney, Agent, or Firm—Beyer Weaver & Thomas LLP

(57) ABSTRACT

An atomizer has a liquid container containing a liquid to be atomized and an oscillator having a cylindrically shaped top part and protruding from the bottom of the liquid container. A pipe or a portion of the inner wall of the liquid container is sufficiently close to the outer surface of the top part of the oscillator so as to form a gap of 3 mm or less such that when the oscillator is caused to oscillate, its vibratory energy causes the liquid to reach the top surface of the oscillator and to be atomized. An inhalator is formed with such an atomizer made detachably attachable to a main housing. A coupling unit with two couplers connected with a cable may be used to attach the atomizer to the inhalator's main housing. A mouthpiece and a mask may be made attachable to the atomizer.

20 Claims, 5 Drawing Sheets

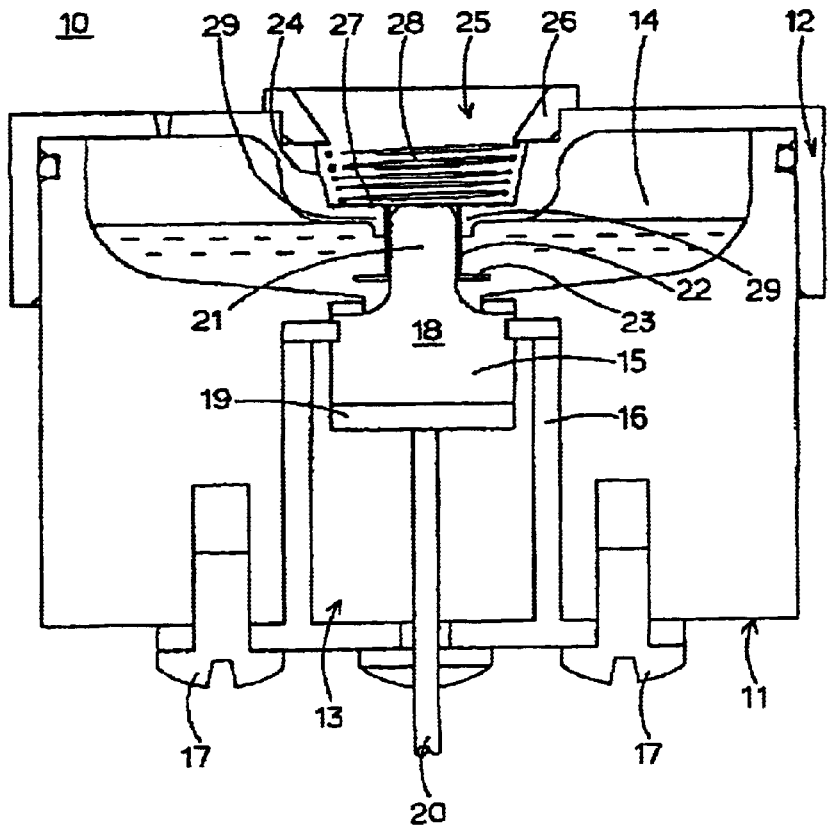
FIG. 1
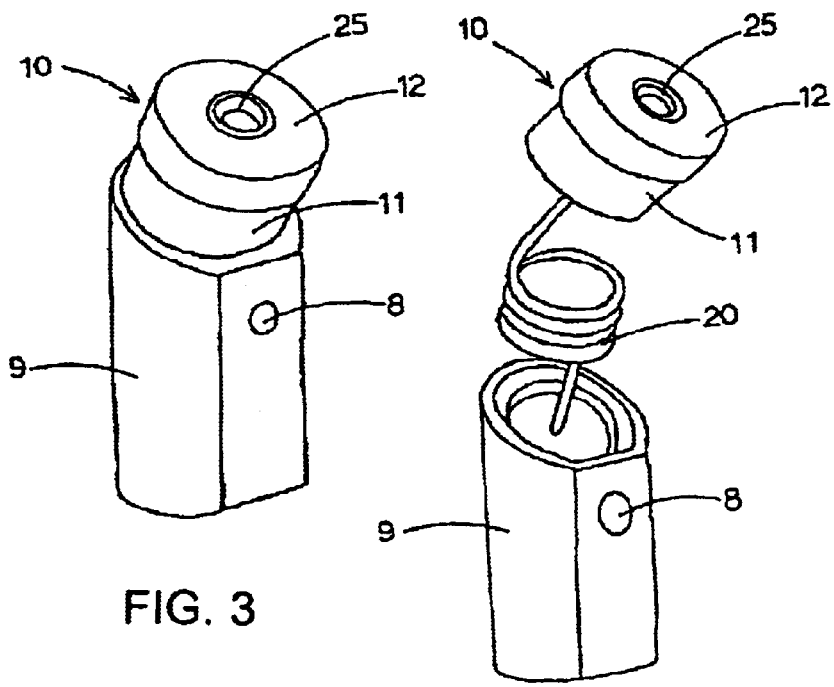
FIG. 3
FIG. 4

ATOMIZER AND INHALATOR USING SAME

BACKGROUND OF THE INVENTION

This invention relates to an atomizer of the type commonly used in an inhalator.

It has been known to produce a portable ultrasonic atomizer by placing a mesh on the oscillating surface of an oscillator to form an atomizing part and supplying there a liquid to be atomized from a liquid supply part. Ultrasonic atomizers of this type are useful because they are compact low-power devices capable of dependably atomizing a liquid chemical to produce droplets of a uniform particle size.

FIG. 9 shows an example of prior art oscillator 1 comprised of a larger-diameter cylindrical part 1a and a small-diameter cylindrical part 1b with an atomizing surface 1c and provided with a liquid supply route 2 which starts from one side part of the larger-diameter part 1a to a center part of the smaller-diameter part 1b and reaches from there to the atomizing surface 1c. A liquid to be atomized is caused to pass through this supply route 2 by means of a pressure pump or the like (not shown) to reach the atomizing surface 1c at the top of the oscillator 1.

Such prior art ultrasonic atomizers are useful but require a separate driving means such as a solenoid for supplying a liquid and are inconvenient in that their operations are complicated and the maintenance is cumbersome because of their complicated structure and shape. Production of an atomizer as shown in FIG. 9 is troublesome because a liquid supply route must be prepared inside a cylindrical oscillator body, and a pressure pump or the like is still needed for supplying a liquid.

SUMMARY OF THE INVENTION

It is therefore an object of this invention in view of the above to provide an improved atomizer with a simple structure and requiring no driving means for supplying a liquid to be atomized.

It is another object of this invention to provide an improved inhalator using such an atomizer which is easier to use than prior art inhalators.

An atomizer embodying this invention, with which the above and other objects can be accomplished, may be characterized as comprising a liquid container containing a liquid to be atomized and an oscillator having a cylindrically shaped top part and protruding from the bottom of the liquid container. A pipe or a portion of the inner wall of the liquid container is sufficiently close to the outer surface of the top part of the oscillator so as to form a gap of 3 mm or less such that when the oscillator is caused to oscillate, its vibratory energy causes the liquid to reach the top surface of the oscillator and to be atomized.

An inhalator according to this invention is characterized as comprising such an atomizer and a main housing. According to a preferred embodiment, the main housing and the atomizer are detachably attachable. A coupling unit with two couplers connected with a cable may be used to attach the atomizer to the inhalator's main housing. A mouthpiece and a mask may be made attachable to the atomizer.

BRIEF DESCRIPTION OF THE DRAWINGS

FIG. 1 is a schematic sectional view of an atomizer embodying this invention.

FIG. 3 is an external view of an inhalator having installed therein the atomizer of this invention.

FIG. 4 is an external view of another inhalator embodying this invention.

Throughout herein, components which are equivalent to each other or at least alike are indicated by same numerals even if they are components of different atomizers or inhalators and may not necessarily be described repetitiously.

DETAILED DESCRIPTION OF THE INVENTION

Figure 2:
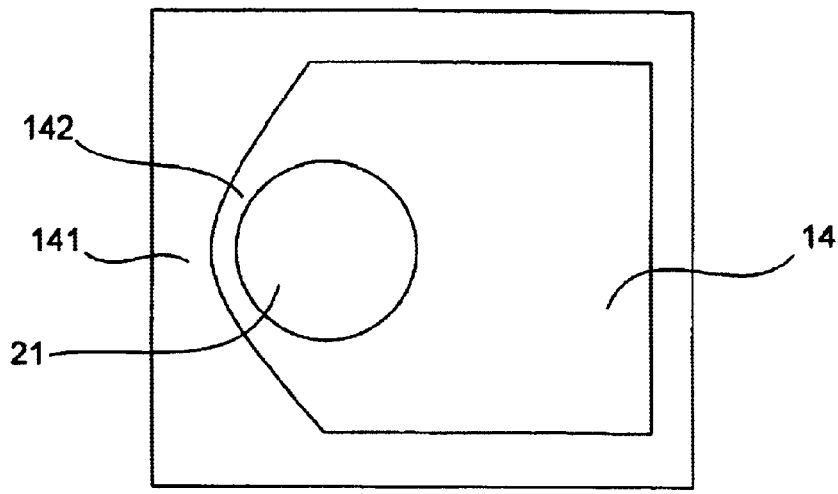
FIG. 2 is a schematic plan view of a portion of an atomizer according to another embodiment of the invention dispensed with a liquid supplying pipe shown in FIG. 1.
Figure 5:
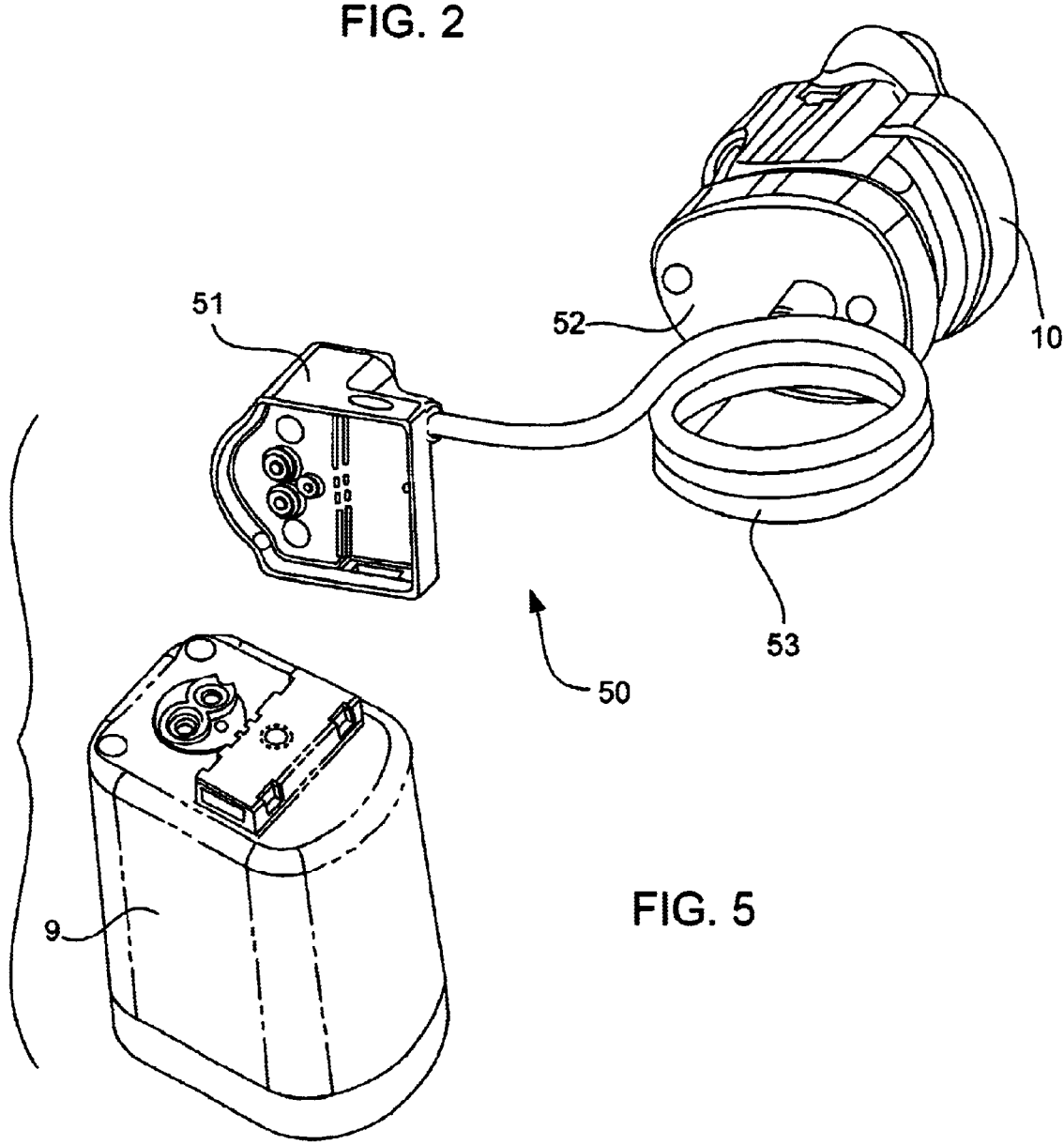
FIGS. 5–8 show still another inhalator embodying this invention.
Figures 6, 7:
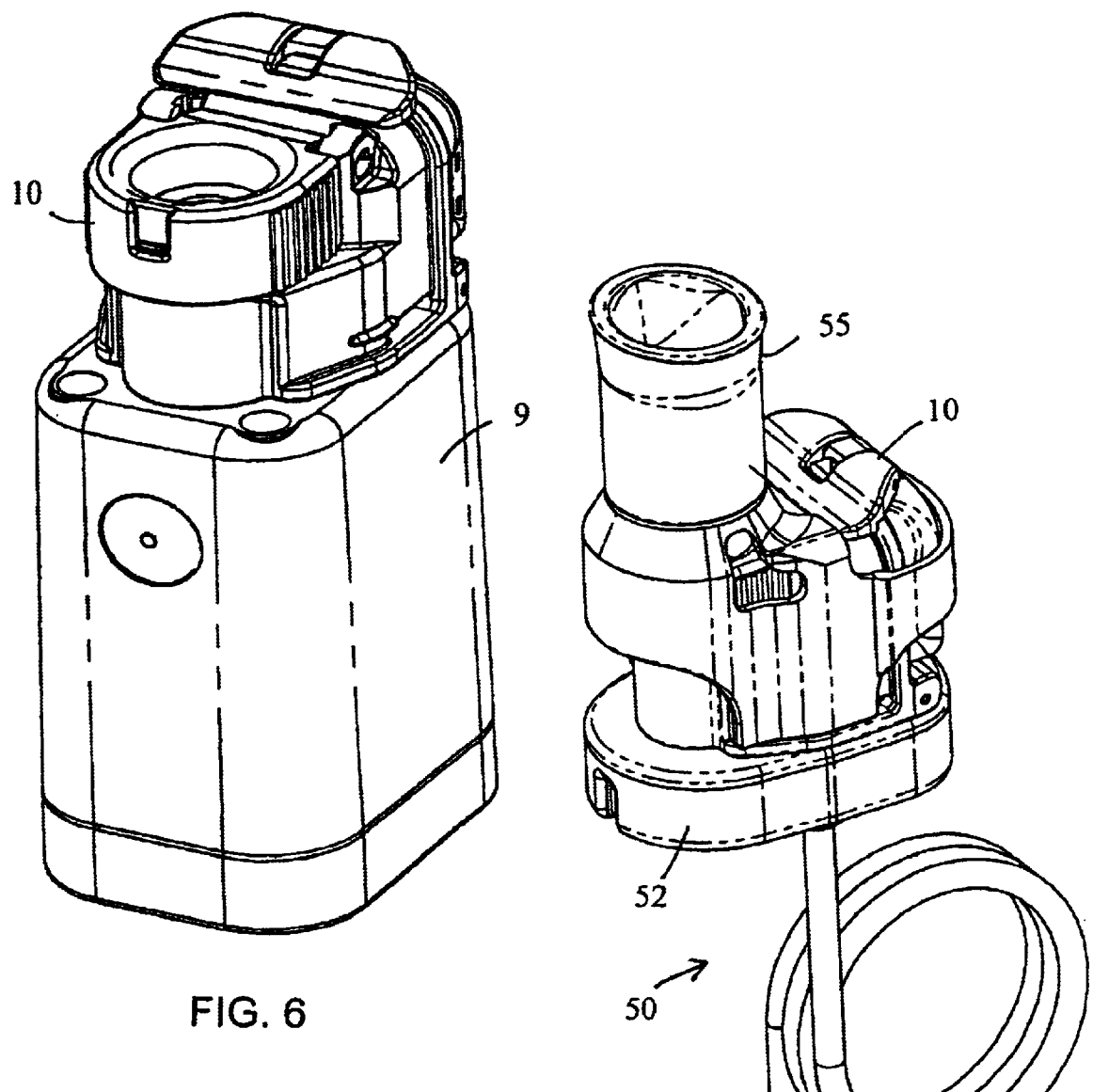
Figure 8:
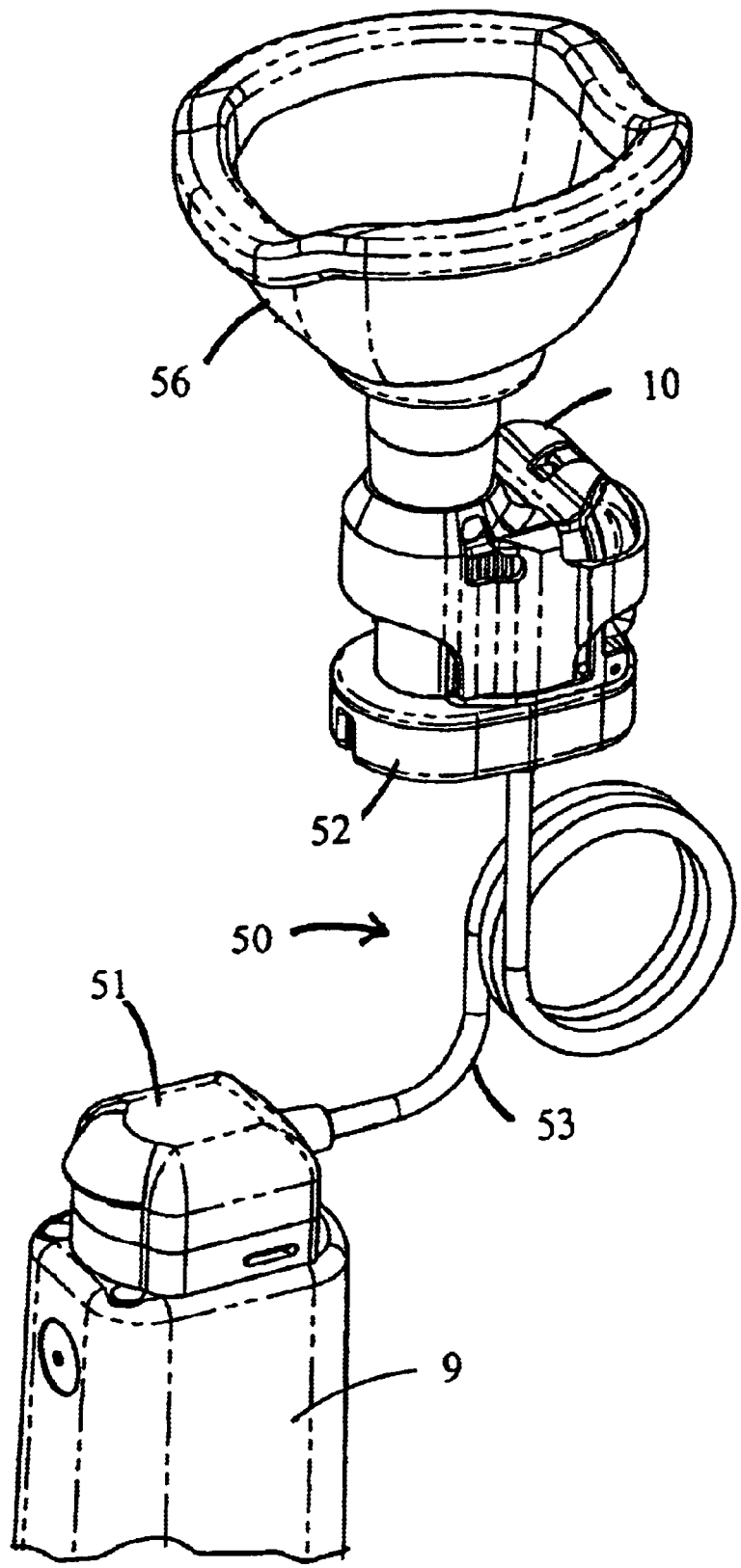
Figure 9:
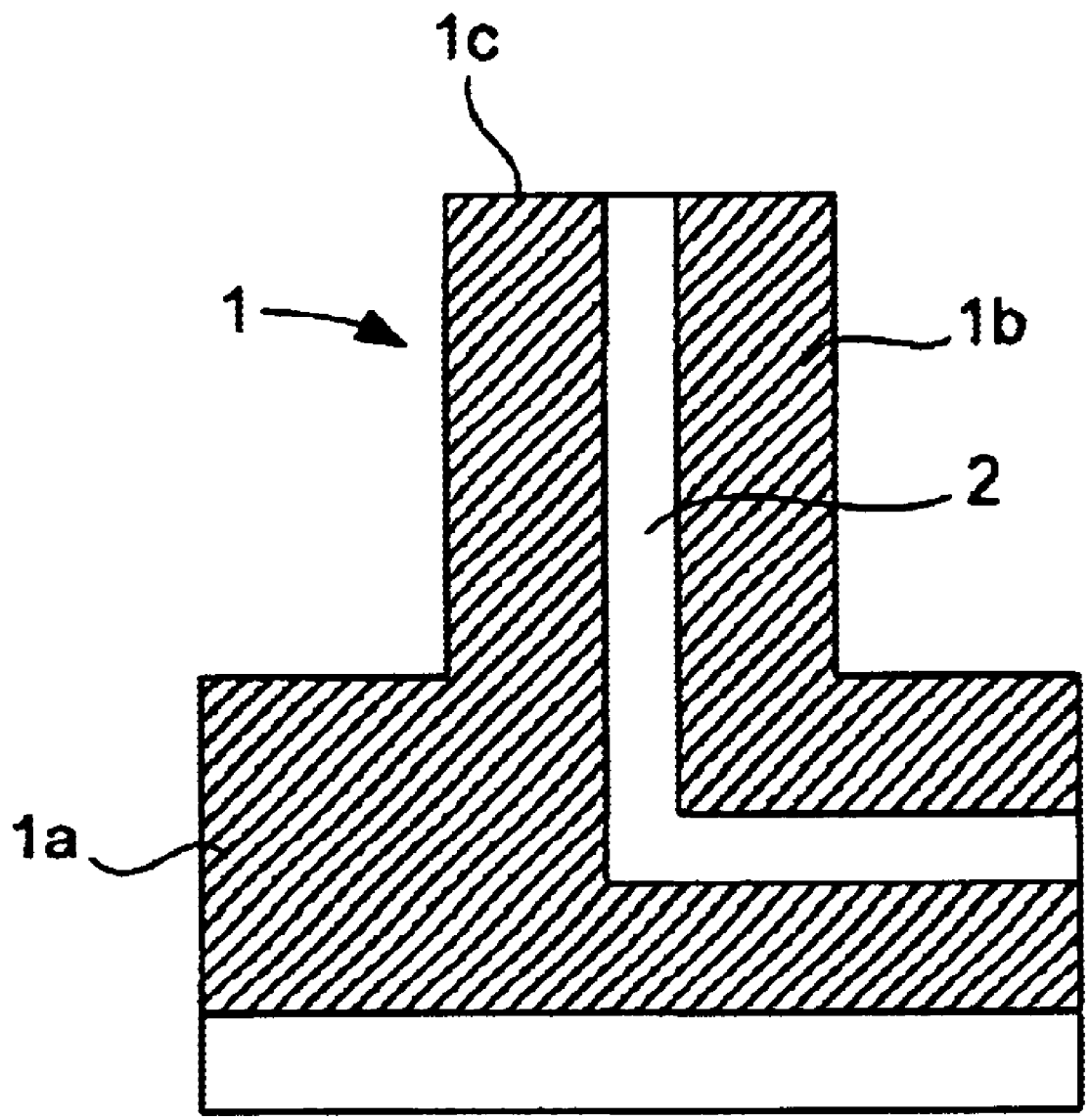
FIG. 9 is a sectional view of an oscillator for a prior art atomizer.

The invention is described next by way of an example. FIG. 1 shows the structure of an atomizer 10 embodying this invention, composed of a casing 11, a cover 12 and an oscillator unit 13. The cover 12 is detachably attachable to the casing 11, and a liquid container 14 for containing a liquid to be atomized is provided at an upper part of the casing 11.

The oscillator unit 13 includes an oscillator 15 of a generally cylindrical shape and a cylindrical supporting member 16 for supporting the oscillator 15. The oscillator unit 13 itself is affixed to the bottom of the casing 11 by means of screws 17. The oscillator 15 is positioned such that its smaller-diameter part 21 protrudes upward into the liquid container 14 when the oscillator unit 13 is thus affixed.

The oscillator 15 is composed of an oscillator body 18 and a piezoelectric element 19. The piezoelectric element 19 may comprise PZT or lithium niobate and is connected to a power source and a circuitry (not shown) by an electrically conductive lead line 20. The oscillator body 18 may comprise a metallic or ceramic material, formed by a method such as sintering, metallic powder injection molding and cutting. The exterior of the smaller-diameter part 21 of the oscillator 15 is covered with a cylindrical liquid supplying pipe 22 which may comprise a metallic material, a thin resin material or a ceramic material. A flange 23 is provided at the lower end of this liquid supplying pipe 22. The purpose of this flange 23 is to provide a small gap with the bottom surface of the liquid container 14 such that even a small quantity of the liquid left at the bottom of the container 14 can be effectively sucked upwards by the vibration of the oscillator 15.

The cover 12 has an opening 24 at its center, provided with an atomizing unit 25. The atomizing unit 25 is composed of a guide wall 26 adapted to be screwed into the opening 24, a mesh 27 placed on top of the top surface of the oscillator 15 and the liquid supplying pipe 22, and a spring 28 serving to push the mesh 27 downward. The liquid supplying pipe 22 is supported by a supporting member 29 provided at the opening 24 of the cover 12.

For using this atomizer, the cover 12 is removed from the casing 11, and after the liquid container 14 is filled with a liquid to be atomized, the cover 12 is attached again to the casing 11. As the atomizer is switched on, the piezoelectric element 19 begins to vibrate, and its vibratory energy propagates from the larger-diameter part 18a to the top end of the smaller-diameter part 21. This vibratory energy causes the liquid inside the container 14 to move upwards between the outer wall of the smaller-diameter part 21 of the oscillator body 18 and the liquid supplying pipe 22 and to reach the top surface of the oscillator body 18. The gap between the outer wall of the smaller-diameter part 21 of the oscillator body 18 and the liquid supplying pipe 22 is preferably less than 0.3 mm such that the capillary effect of the liquid in the gap will favorably contribute to the efficient upward motion of the liquid to the top oscillator body 18. The liquid thus supplied onto the top surface of the oscillator body 18 is atomized by the vibration of the top surface and is ejected out through the mesh 27 and the guide wall 26.

With an atomizer 10 thus structured, there is no need for a solenoid or a pressure pump for supplying the liquid because the liquid is supplied upward by the vibratory energy to the atomizing unit 25 between the outer wall of the smaller-diameter part 21 of the oscillator body 18 and the liquid supplying pipe 22. The flange 23 at the lower end of this liquid supplying pipe 22 serves to provide another supply route for the liquid between itself and the bottom surface of the liquid container 14, thereby improving the efficiency of liquid supply and reducing the amount of liquid left.

Since the liquid supplying pipe 22 described above is for the purpose of providing a narrow passage around the smaller-diameter part 21 of the oscillator body 18 for assisting the liquid inside the liquid container 14 to pass through to move upward with the energy of vibration of the oscillator body 18, it is hereinafter also referred to more generally as the “gap-forming member”, the space between the outer surface of the smaller-diameter part 21 of the oscillator body 18 and the liquid-supplying pipe 22 being referred to as the “gap”. According to another embodiment of the present invention intended to reduce the production cost of the atomizer, the liquid-supplying pipe 22 may be dispensed with. FIG. 2 shows schematically an example of such an embodiment characterized as using a portion of the inner wall of the liquid container 14 as the gap-forming member. Explained more in detail with reference to FIG. 2, a portion 141 of the inner wall of the liquid container 14 is designed to form a gap 142 of less than 3 mm (for example, about 2 mm) with a portion of the cylindrical outer surface of the smaller-diameter part 21 of the oscillator body 18.

FIG. 3 shows an inhalator having installed therein an atomizer 10 as described above. Numeral 9 indicates the main body of the inhalator. The atomizer 10 is formed integrally and in a sloped relationship with the inhalator main body 9 for the convenience of a user who may choose to keep the inhalator standing while using it. The circuitry and the power source for operating the piezoelectric element 19 are contained inside the inhalator main body 9. A start switch 8 is on the inhalator main body 9.

FIG. 4 shows another inhalator characterized wherein the inhalator main body 8 and the atomizer 10 are not integrally formed but are detachable one from the other. This embodiment is advantageous in that the atomization unit 15 itself becomes lighter, and the user does not become tired after holding it in hand for a long time.

The invention has been described above only by way of a limited number of embodiment but they are not intended to limit the scope of the invention. Many modifications and variations are possible within the scope of the invention. For example, the atomizer 10 need not be in a sloped relationship with the inhalator main body 9. Since the inhalator according to this invention is much lighter than conventional inhalators, the user may not always leave it standing by itself, say, on the top of a table, when using it. Instead, the user may choose to carry it by hand. For such a user, it is not necessarily advantageous to have the atomizer in a sloped relationship with the inhalator main body. Since the inhalator main body is likely to be tilted when being held by the user’s hand while it is being used, it may be advantageous to position the oscillator 15 not at the center of the liquid container but closer to a portion of its inner wall, as shown in FIG. 2. If the atomizer 10 is tilted while being used, whether attached to or detached from the inhalator main body 9, the liquid remaining inside the container 14 tends to fill the gap 142. This makes it easier for the liquid to reach the top of the oscillator body 18 even if the gap 142 is too large for the capillary effect to be effective. A further advantage of the embodiment shown in FIG. 2 is that the gap 142 is less likely to be clogged with dust particles or the like because of its larger width and that the atomizer 10 is easier to wash in the absence of the liquid supply pipe 22.

FIGS. 5–8 show an inhalator according to still another embodiment characterized as having a coupling unit 50 with a coupler 51 for attaching to the inhalator main body 9 and another coupler for connecting to the atomizer 10, both couplers 51 and 52 being connected with a cable 53. FIG. 5 shows the coupler unit 50 detached from the inhalator main body 9 and also from the atomizer 10. FIG. 6 shows the coupler unit 50 dispensed with, having the atomizer 10 directly coupled to the inhalator 9. FIG. 7 shows a mouthpiece 55 attached to the atomizer 10, and FIG. 8 shows a face mask 56 attached to the atomizer 10.

What is claimed is:

1. An atomizer comprising:

a liquid container containing a liquid;

an oscillator having a cylindrically shaped top part, said top part having a top surface and protruding into said liquid container;

a gap-forming member disposed proximally to said top part of said oscillator to provide a gap in between for allowing said liquid to pass through;

means for causing said oscillator to oscillate and said liquid to thereby reach said top surface through said gap and to be atomized; and a casing containing said liquid container and said oscillator therein.

2. The atomizer of claim 1 further comprising a mesh placed on said top part of said oscillator.

3. The atomizer of claim 1 wherein said gap-forming member is a pipe which covers said top part of said oscillator.

4. The atomizer of claim 3 wherein said pipe has a flange extending outward.

5. The atomizer of claim 1 wherein said gap-forming member is a portion of an inner wall of said liquid container.

6. The atomizer of claim 5 wherein said gap is less than 3 mm.

7. An inhalator comprising a housing and an atomizer which are connected to each other, said atomizer comprising:

a liquid container containing a liquid;

an oscillator having a cylindrically shaped top part, said top part having a top surface and protruding into said liquid container;

a gap-forming member disposed proximally to said top part of said oscillator to provide a gap in between for allowing said liquid to pass through;

means for causing said oscillator to oscillate and said liquid to thereby reach said top surface through said gap and to be atomized; and a casing containing said liquid container and said oscillator therein.

8. The inhalator of claim 7 further comprising a coupling unit having couplers connected to each other by a cable, one of said couplers being detachably attachable to said housing, the other of said couplers being detachably attachable to said atomizer.

9. The inhalator of claim 8 wherein said housing and said atomizer are directly attachable to each other without said coupling unit.

10. The inhalator of claim 9 wherein said gap-forming member is a pipe which covers said top of part of said oscillator.

11. The inhalator of claim 9 wherein said pipe has a flange extending outward.

12. The inhalator of claim 9 wherein said gap-forming member is a portion of an inner wall of said liquid container.

13. The inhalator of claim 9 further comprising a coupling unit including a first coupler, a second coupler and an electrical cable connecting said first and second couplers, said first coupler being detachably attachable to said housing and said second coupler being detachably attachable to said atomizer.

14. The inhalator of claim 7 further comprising a mesh placed on said top part of said oscillator.

15. The inhalator of claim 7 wherein said gap-forming member is a pipe which covers said lop of part of said oscillator.

16. The inhalator of claim 13 wherein said gap is less than 0.3 mm.

17. The inhalator of claim 7 wherein said pipe has a flange extending outward.

18. The inhalator of claim 7 wherein said gap-forming member is a portion of an inner wall of said liquid container.

19. The inhalator of claim 18 wherein said gap is less than 3 mm.

20. The inhalator of claim 7 further comprising a coupling unit including a first coupler, a second coupler and an electrical cable connecting said first and second couplers, said first coupler being detachably attachable to said housing and said second coupler being detachably attachable to said atomizer.

* * * * *